United States Patent
Bradway et al.

(10) Patent No.: US 10,709,543 B2
(45) Date of Patent: Jul. 14, 2020

(54) NON-CYLINDRICAL MESH TOP STENT WITH TWISTED SECTIONS

(71) Applicants: Cook Medical Technologies, LLC, Bloomington, IN (US); Emily Bell Gibbons, Bloomington, IN (US)

(72) Inventors: Ryan C. Bradway, Tacoma, WA (US); Jarin A. Kratzberg, Lafayette, IN (US); William S. Gibbons, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 70 days.

(21) Appl. No.: 16/038,833

(22) Filed: Jul. 18, 2018

(65) Prior Publication Data
US 2019/0021841 A1     Jan. 24, 2019

Related U.S. Application Data

(60) Provisional application No. 62/534,520, filed on Jul. 19, 2017.

(51) Int. Cl.
    *A61F 2/07*          (2013.01)
    *A61F 2/90*          (2013.01)
    (Continued)

(52) U.S. Cl.
    CPC .................. *A61F 2/07* (2013.01); *A61F 2/90* (2013.01); *A61F 2/88* (2013.01); *A61F 2/92* (2013.01);
    (Continued)

(58) Field of Classification Search
    CPC ...... A61F 2/07; A61F 2/88; A61F 2/89; A61F 2/90; A61F 2/92; A61F 2002/061;
    (Continued)

(56) References Cited

U.S. PATENT DOCUMENTS

| 6,099,558 A | 8/2000 | White et al. |
| 6,241,757 B1 | 6/2001 | An et al. |

(Continued)

FOREIGN PATENT DOCUMENTS

| CN | 102125475 A | 7/2011 |
| DE | 102014115337 A1 | 4/2016 |

(Continued)

OTHER PUBLICATIONS

Communication from EP Application No. 18275102.4, dated Jul. 29, 2019, 4 pages.

(Continued)

*Primary Examiner* — Thomas Sweet
*Assistant Examiner* — Tiffany P Shipmon
(74) *Attorney, Agent, or Firm* — Brinks Gilson & Lione

(57) ABSTRACT

A stent is provided having a plurality of intersecting elongated members arranged to form a plurality of cells, the plurality of cells defining an elongated tube with a lumen running therethrough. The elongated tube has first, second, and third sections, the first section having a substantially first diameter and the third section having a substantially constant second diameter that is larger than the substantially constant first diameter of the first section, wherein the diameter of the second section transitions from the first diameter to the second diameter. Each of the plurality of cells within the first section have a pitch that is tighter than each of the plurality of cells within the second and third sections. In the second section, the plurality of intersecting elongated members includes a plurality of pairs of elongated members, wherein each pair of elongated members includes two adjacent elongated members twisted axially around each other.

12 Claims, 8 Drawing Sheets

(51) Int. Cl.
  *A61F 2/88* (2006.01)
  *A61F 2/92* (2013.01)
  *A61F 2/82* (2013.01)
(52) U.S. Cl.
  CPC . *A61F 2002/823* (2013.01); *A61F 2230/0004* (2013.01); *A61F 2230/0065* (2013.01); *A61F 2230/0069* (2013.01); *A61F 2250/0018* (2013.01); *A61F 2250/0039* (2013.01)
(58) Field of Classification Search
  CPC .......... A61F 2002/067; A61F 2002/826; A61F 2230/0019; A61F 2240/001
  See application file for complete search history.

(56) References Cited

U.S. PATENT DOCUMENTS

| | | | |
|---|---|---|---|
| 6,585,758 | B1 | 7/2003 | Chouinard et al. |
| 7,048,014 | B2 | 5/2006 | Hyodoh et al. |
| 7,771,466 | B2 | 8/2010 | Chouinard et al. |
| 8,002,816 | B2 | 8/2011 | Greenberg |
| 8,491,647 | B2 | 7/2013 | Colgan et al. |
| 8,956,400 | B2 | 2/2015 | Beach et al. |
| 2006/0195172 | A1 | 8/2006 | Luo et al. |
| 2007/0043435 | A1 | 2/2007 | Seguin et al. |
| 2007/0073388 | A1 | 3/2007 | Krolik et al. |
| 2008/0319552 | A1 | 12/2008 | Styrc |
| 2009/0270965 | A1 | 10/2009 | Sinha et al. |
| 2011/0060398 | A1* | 3/2011 | Tupil, Sr. .................. A61F 2/07 623/1.15 |
| 2011/0093002 | A1 | 4/2011 | Rucker et al. |
| 2012/0046726 | A1 | 2/2012 | Chuter |
| 2014/0060691 | A1 | 3/2014 | Du |
| 2014/0277370 | A1 | 9/2014 | Brocker et al. |
| 2014/0277573 | A1* | 9/2014 | Gill .......................... A61F 2/90 623/23.68 |
| 2014/0296966 | A1 | 10/2014 | Braido et al. |
| 2014/0316513 | A1 | 10/2014 | Tang |
| 2015/0148883 | A1 | 5/2015 | Hyodoh |
| 2015/0157477 | A1 | 6/2015 | Shahriari |
| 2017/0071766 | A1 | 3/2017 | During et al. |
| 2017/0304093 | A1* | 10/2017 | During ....................... A61F 2/90 |

FOREIGN PATENT DOCUMENTS

| | | |
|---|---|---|
| EP | 2005918 A1 | 12/2008 |
| EP | 3326582 A1 | 5/2018 |
| WO | WO 2009/094188 A2 | 7/2009 |

OTHER PUBLICATIONS

Qingsheng Lu, et al., "Endovascular Repair of Ascending Aortic Dissection—A Novel Treatment Option for Patients Judged Unfit for Direct Surgical Repair," *Clinical Research: Vascular Disease*, vol. 61, Issue 18, May 2013, 8 pages.

European Search Report for related EP Application No. 18275101, dated Nov. 21, 2018, 9 pages.

European Search Report for corresponding EP Application No. 18275102, dated Nov. 21, 2018, 8 pages.

* cited by examiner

NON-CYLINDRICAL MESH TOP STENT WITH TWISTED SECTIONS

RELATED APPLICATIONS

The application claims the benefit of the filing date under 35 U.S.C. § 119(e) of Provisional U.S. Patent Application Ser. No. 62/534,520, filed Jul. 19, 2017, which is hereby incorporated by reference in its entirety.

FIELD

The present disclosure relates to medical devices and more specifically to stents used to treat a diseased vessel or region of vessels.

BACKGROUND

The statements in this section merely provide background information related to the present disclosure and may not constitute prior art.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture, resulting in an aortic dissection.

One treatment option for weakened, aneurysmal, or ruptured vessels is the use of stent grafts, placed either surgically or endovascularly. A stent graft may be, for example, a tubular structure that is placed into a body lumen, such as the aorta, to, for example, span a weakened area or to maintain patency of the body lumen. When treating aortic aneurysms or dissections, a stent graft is generally placed within the damaged portion of the aorta to bypass the weakened area of the aorta or to seal a tear (dissection) in the aorta, thereby reestablishing a closed pathway for blood to flow through.

While aortic aneurysms and dissections can occur along the length of the aorta, they are particularly difficult to treat when occurring in the ascending aorta near the sinotubular junction. Conventional seal stents often do not provide an adequate seal near the sinotubular junction because of its unusual anatomy. While the ascending aorta is substantially cylindrical in shape, the sinotubular junction marks a transition point from this cylindrical anatomy to the annular shape of the aortic root. Thus, the transition point of the sinotubular junction sees an anatomical change in both size and diameter. Due to these anatomical changes, stent grafts positioned near the sinotubular junction have issues with leakage and sufficient sealing of the aorta. Thus, it is desirable to provide a stent graft that can provide an adequate seal in the ascending aorta near the sinotubular junction.

SUMMARY

In one form of the present disclosure, a stent is provided. The stent comprises a plurality of intersecting elongated members arranged to form a plurality of cells, the plurality of cells defining an elongated tube with a lumen running therethrough. Further, the elongated tube comprises first, second, and third sections, the first section having a substantially constant first diameter and the third section having a substantially constant second diameter that is larger than the substantially constant first diameter of the first section, wherein the diameter of the second section transitions from the first diameter to the second diameter. Additionally, a proximal end of the third section of the stent comprises a plurality of rounded ends formed by the plurality of intersecting elongated members. Also, each of the plurality of cells within the first section have a pitch that is tighter than each of the plurality of cells within the second and third sections. Further, in the second section of the stent, the plurality of intersecting elongated members comprise a plurality of pairs of elongated members, wherein each pair of elongated members comprises two adjacent elongated members twisted axially around each other.

The stent may further comprise a delivery configuration and an expanded configuration, wherein the stent is radially compressed to a smaller outer diameter in the delivery configuration when compared to the expanded configuration. The stent may also be self-expanding. The stent may also include a graft connected to the stent. Further, the graft may cover the first section of the elongated tube of the stent by not the second and third sections.

In another form of the disclosure, a stent is provided. The stent comprises a plurality of intersecting elongated members arranged to form a plurality of cells, the plurality of cells defining an elongated tube with a lumen running therethrough. Further, the elongated tube comprises first, second, and third sections, the first section having a first diameter and the third section having a second diameter that is larger than the first diameter of the first section, wherein the diameter of the second section transitions from the first diameter to the second diameter. Additionally, in the second section, the plurality of intersecting elongated members comprises a plurality of pairs of elongated members, wherein each pair of elongated members comprises two adjacent elongated members twisted axially around each other.

In yet another embodiment of the disclosure, a method of placing a stent graft is provided. The method comprises introducing a stent graft into an aorta of a patient with the stent graft in a compressed, delivery configuration, the stent graft comprising a stent comprising a plurality of intersecting elongated members arranged to form a plurality of cells, the plurality of cells defining an elongated tube with a lumen running therethrough, wherein the elongated tube comprises first, second, and third sections, the first section having a substantially constant first diameter and the third section having a substantially constant second diameter that is larger than the substantially constant first diameter of the first section, wherein the diameter of the second section transitions from the first diameter to the second diameter, wherein in the second section, the plurality of intersecting elongated members comprises a plurality of pairs of elongated members, wherein each of the plurality of cells within the first section have a pitch that is tighter than each of the plurality of cells within the second and third sections, wherein each pair of elongated members comprises two adjacent elongated members twisted axially around each other, the stent graft further comprising a graft attached to the stent. The method further comprises positioning the stent graft near a sinotubular junction of the aorta and deploying the stent graft from the delivery configuration to an expanded configuration in which the stent graft expands radially outward such that the second and third sections of the stent are disposed proximal the sinotubular junction of the aorta Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
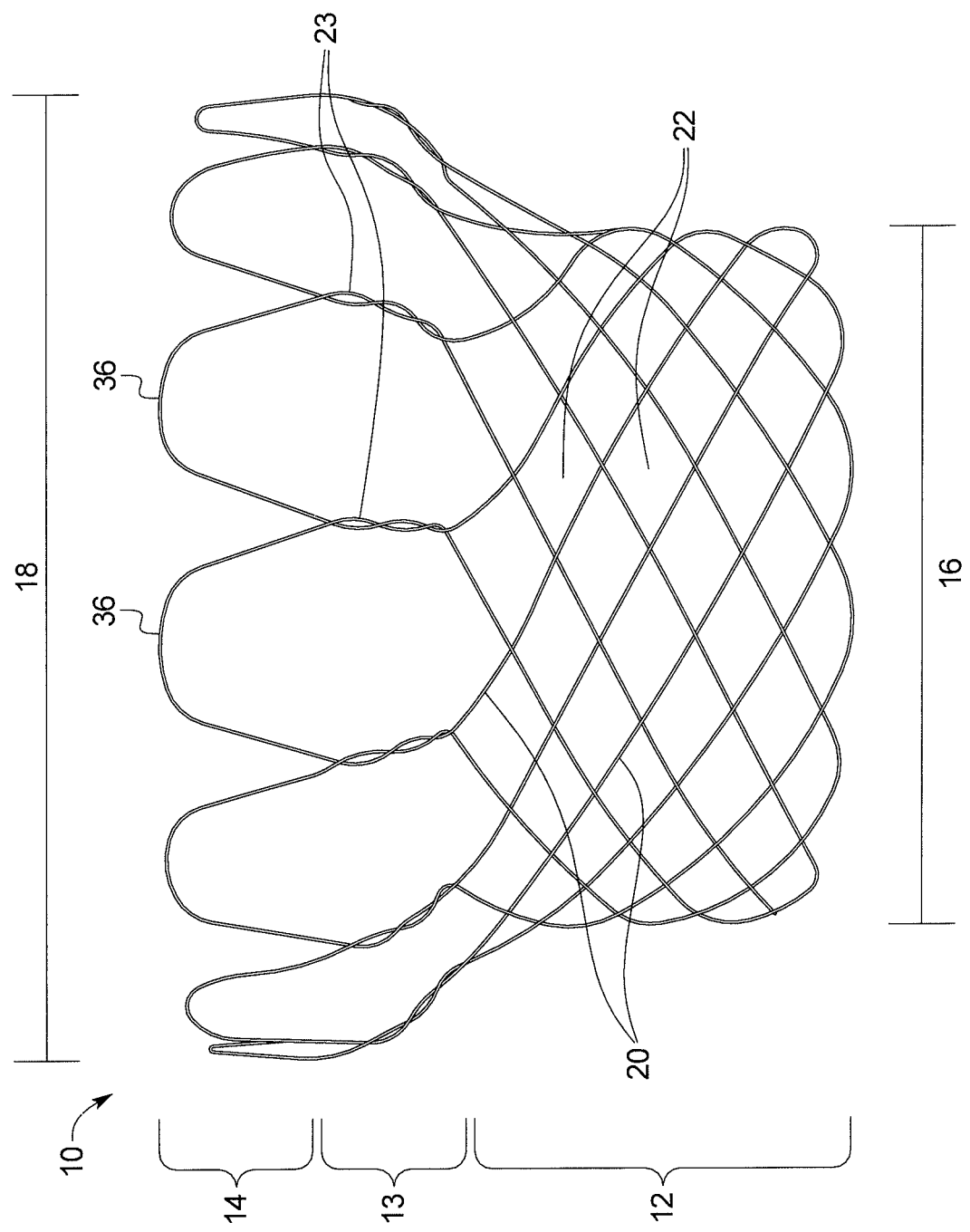
FIG. 1 is a partial side view of a stent in accordance with the teachings of the present disclosure.

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

In the present application, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first), and the outflow end (that end from which the fluid exits).

Figure 2:
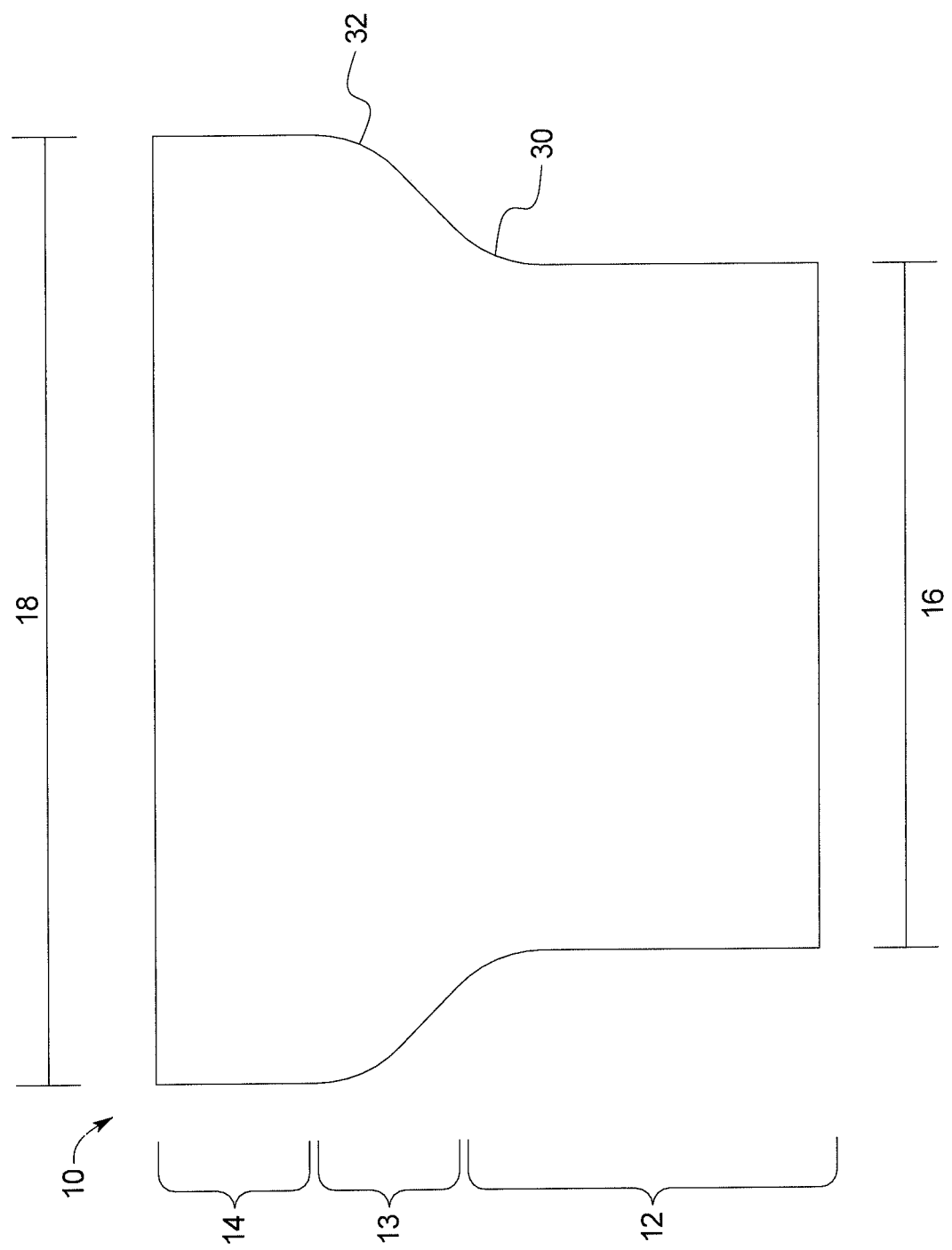
FIG. 2 is a partial profile view of a stent.

FIG. 1 shows a partial view of stent 10. The stent 10 may include three sections: a first section 12, a second section 13, and a third section 14. The first section 12 may have a substantially constant outer diameter 16. The second section 13 may transition from the constant outer diameter 16 of the first section to a larger outer diameter 18. The third section 14 may have a substantially constant outer diameter 18. The transition in the second section 13 from the smaller outer diameter 16 of the first section to the larger outer diameter 18 of the third section 14 may be gradual as shown in FIG. 1. Further, the transition in the second section 13 from the small outer diameter 16 to the larger outer diameter 18 may be substantially or wholly continuous. For example, as shown by the partial profile of the stent 10 in FIG. 2, a first concave curvature 30 of the second section 13 may begin the transition from the smaller outer diameter 16 towards the larger outer diameter 18. Then, a second, convex curvature 32 of the second section 13 may transition from the first, concave curvature 30 to the larger outer diameter 18 of the third section 14. While the first, second, and third sections 12, 14 of the stent 10 in the present embodiment are arranged as described above, the stent 10 is not limited to this shape. For example, the stent 10 may include further sections of varying diameters.

Referring back to FIG. 1, the stent 10 may be made of a series of intersecting wires or elongated member 20 connected to each other that form cells 22 of varying sizes and shapes. For example, the stent 10 may be braided. The wire ends may be back braided and overlapped in the first section where they may be welded or soldered together. The size of the cells 22 may be varied by changing how closely together the elongated members 20 are assembled. Assembling the elongated members 20 closely together results in smaller cells 22, otherwise known as a tighter pitch. Conversely, assembling the elongated members 20 further apart results in larger cells 22, otherwise known as a looser pitch. By varying the size of the cells 22, the properties of the stent 10 may be varied. For example, cells 22 with a tighter pitch may have a greater radial force, thus allowing those cells 22 to provide more support to a body lumen. On the other hand, cells 22 with a looser pitch have a lesser radial force. However, cells 22 with a looser pitch allow a stent to elastically compress and expand between a larger outer diameter and a smaller outer diameter when compared to cells 22 with a tighter pitch, thus allowing the stent to be compressed into a delivery configuration with a smaller overall profile.

As shown, the cells 22 in the first section 12 are smaller than the cells 22 in the third section 14. The tighter pitch in the first section 12 allows for a greater radial force, thus providing additional radial support to the body lumen along the length of the first section 12. Since the third section 14 expands to a greater outer diameter 18 than the first section 12, a looser pitch allows the third section 14 to be radially compressed more easily into a delivery configuration. The proximal ends 36 of stent 10 may be rounded, thus limiting any potential puncturing of, or other trauma to, the walls of the body lumen. Although the first section 12 of the stent 10 is described as having a tighter pitch than the third section 14, this is only one example of varying cell size to achieve a varying pitch. A variety of other pitch variation along the length of the stent 10 is contemplated.

Figure 3:
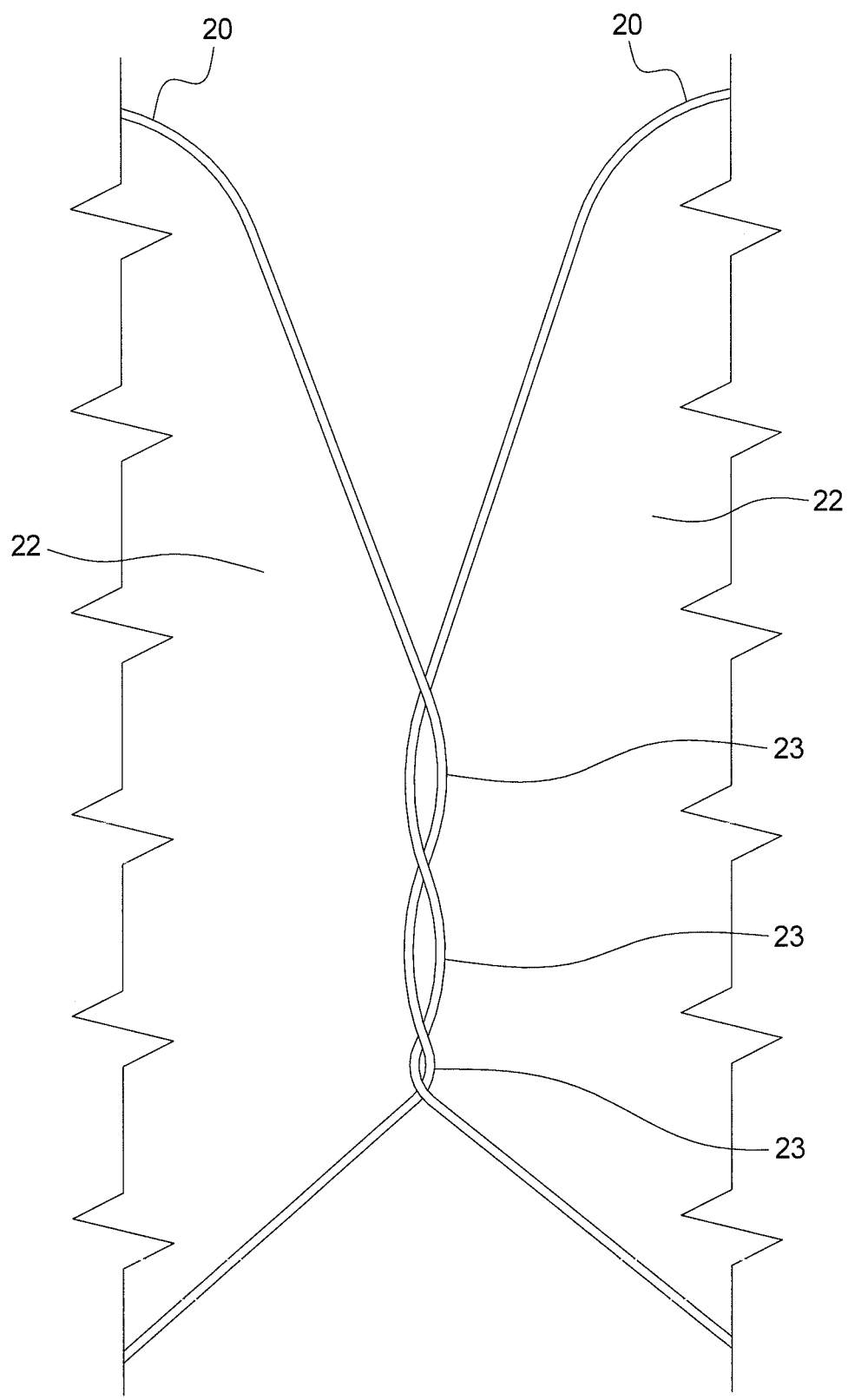
FIG. 3 is a detailed view of a twisted section of a stent.

To accomplish a larger pitch in the second and third sections 13, 14 and a smaller pitch in the first section 12, the second section 13 transitions from a smaller outside diameter 16 to a larger outside diameter 18, as discussed in detail above. To further accomplish the varying pitches, the second section 13 may also include twists 23 in adjacent elongated members 20 (shown in more detail in FIG. 3). Essentially, two adjacent elongated members 20 may be axially twisted around each other to form one or more twists 23. Around the entire circumference of the stent 10, groups of two elongated members 20 each may be twisted together into twists 23, as shown in FIG. 1. In this embodiment, and as shown in more detail in FIG. 3, each group of two elongated members 20 are twisted around each other three times into three twists 23. However, any number of twists 23 may be used, including one or two twists for each group of two elongated members 20. As shown, the twists are in the axial direction and have no free ends. Solder joints (not shown) may be included on the twists to increase radial force.

Figure 4:
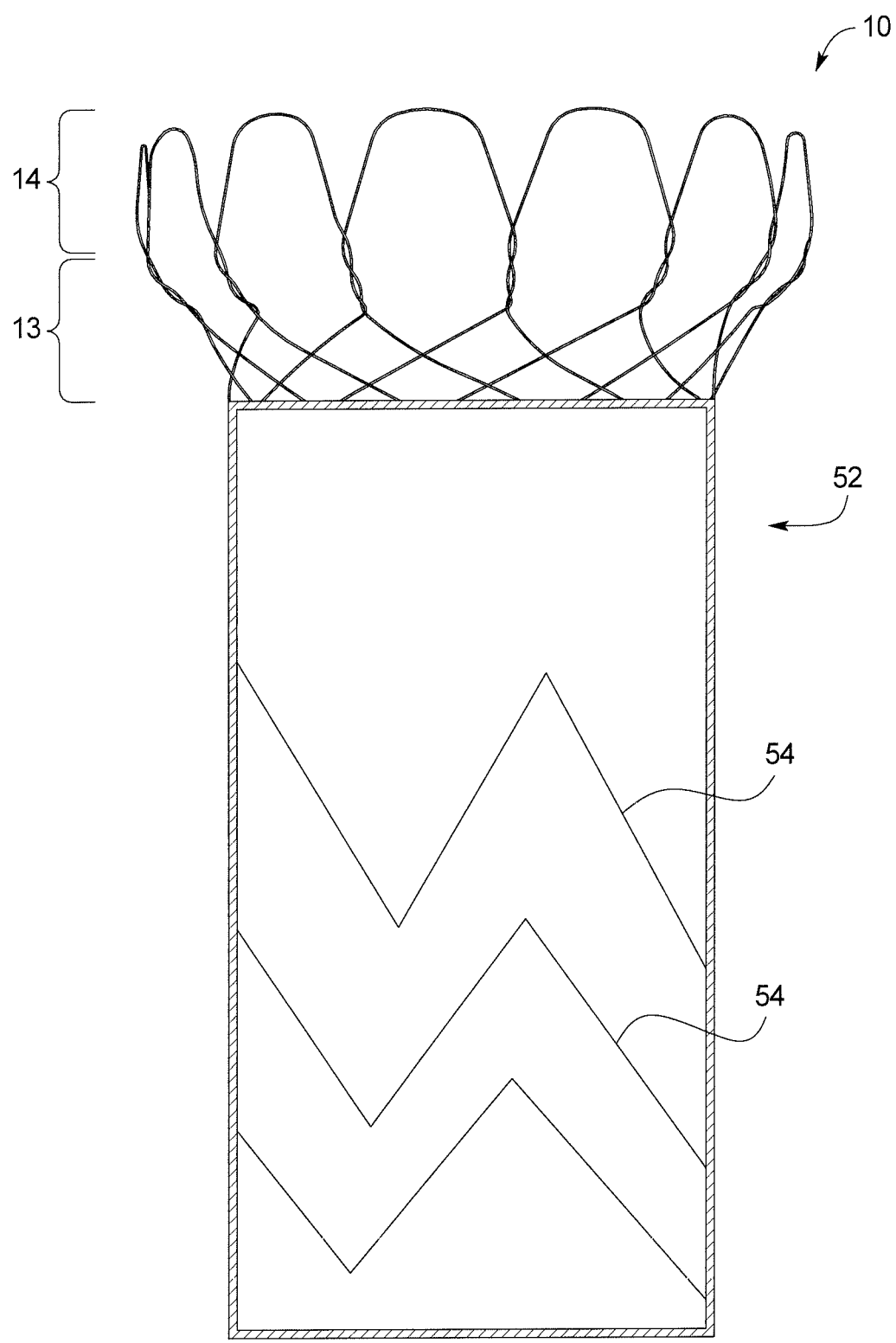
FIG. 4 is a side view of a stent graft.

The portion of the stent 10 shown may be only one portion of a stent graft system. For example, as shown in FIG. 4, a stent graft 50 may include the stent 10, a graft 52, and a body stent 54. The graft 52 may be a generally cylindrical piece of material that has a lumen (not shown) running therethrough. The first section 12, or most of the first section 12, of the stent 10 may be disposed within the lumen of the graft 52 while the second and third sections 13, 14 of the stent 10 may extend outside of the lumen of the graft 52. The first section 12 of the stent 10 may be sewn onto or otherwise attached to the graft 52. While the first section 12 of the stent 10 shown in FIG. 4 is disposed entirely or mostly within the lumen of the graft 52, it may also be attached to the outside surface of the graft 52 as well. The body stent 54 may be a variety of stent designs, including but not limited to: Z-stents, annular stents, and helical stents. The body stent 54 may be sewn or otherwise attached to the graft 52, either within or outside of the lumen of the graft 52. While this embodiment describes a stent graft 50 with a separate stent 10 and body stent 54, the system could also include a single stent with the properties of both the stent 10 and body stent 54 rather than two separate stents.

Figure 5:
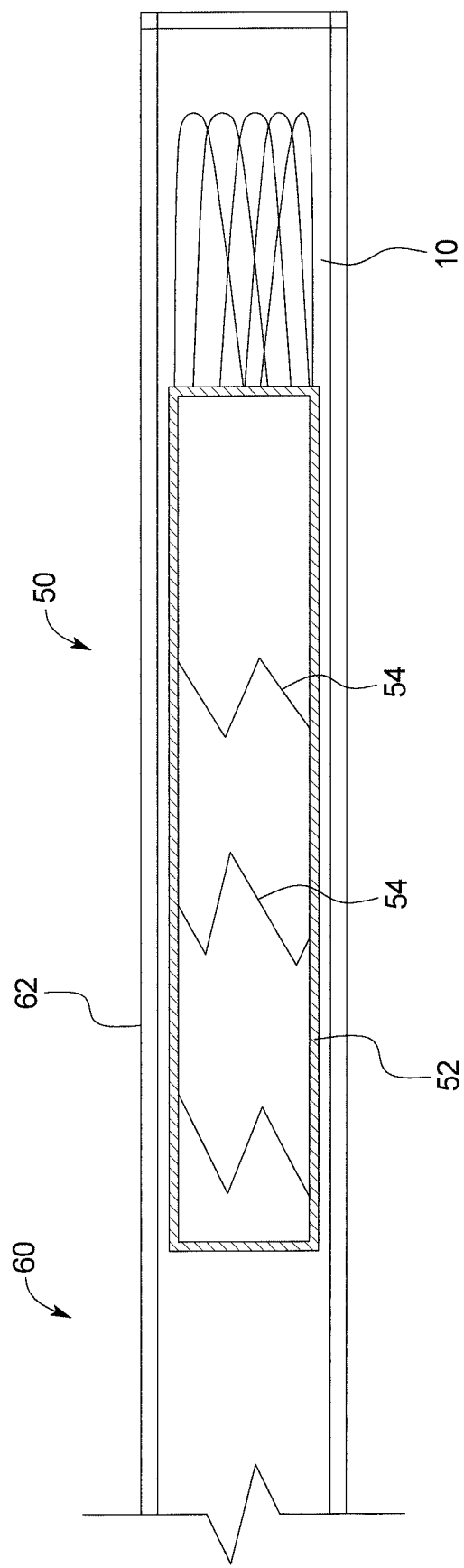
FIG. 5 is a side view of a stent graft with a delivery system.

The entire stent graft 50, in use, may be may be alternatively moved between a delivery configuration in which the stent graft 50 is radially compressed (FIG. 4) to an expanded configuration in which the stent graft 50 is radially expanded (FIG. 5). The stent graft 50 in the present embodiment may be self-expanding, meaning the stent graft's 50 natural state is the expanded configuration. The stent graft 50 is then elastically, radially compressed to the delivery configuration via a delivery device. When the delivery device is removed from the stent graft 50, the stent graft 50 naturally expands back to the expanded configuration. While the present embodiment utilizes self-expanding properties, other stents may be used, including balloon-expandable stents.

The stent 10 and body stent 54 may each be made of a variety of biocompatible materials, including but not limited to: stainless steel, nitinol, or cobalt-chrome alloys, amorphous metals, tantalum, platinum, gold, titanium, and non-metallic materials such as thermoplastics and other polymers. The graft 52 may be made of a variety of biocompatible materials, including but not limited to: expanded polytetrafluoroethylene (ePTFE), polytetrafluoroethylene (PTFE), silicone, polyurethane, polyamide (nylon), as well as other flexible biocompatible materials. The graft 52 also can be made of known fabric graft materials such as woven polyester, polyetherurethanes, or polyethylene. The graft 52 also may include a bioremodelable material such as reconstituted or naturally-derived collagenous materials, extracellular matrix (ECM) material, submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, uterine submucosa, or other suitable materials.

In use, the stent graft 50 may be radially compressed into the delivery configuration via a delivery system 60 as shown in FIG. 5. The delivery system 60 may include a wide variety of stent delivery mechanisms; however, in this exemplary embodiment the delivery system 60 includes a retractable catheter 62 with a lumen within which the stent graft 50 is held in the delivery configuration. The stent graft 50 may be disposed at the proximal end of the lumen of the catheter 62.

Figure 6:
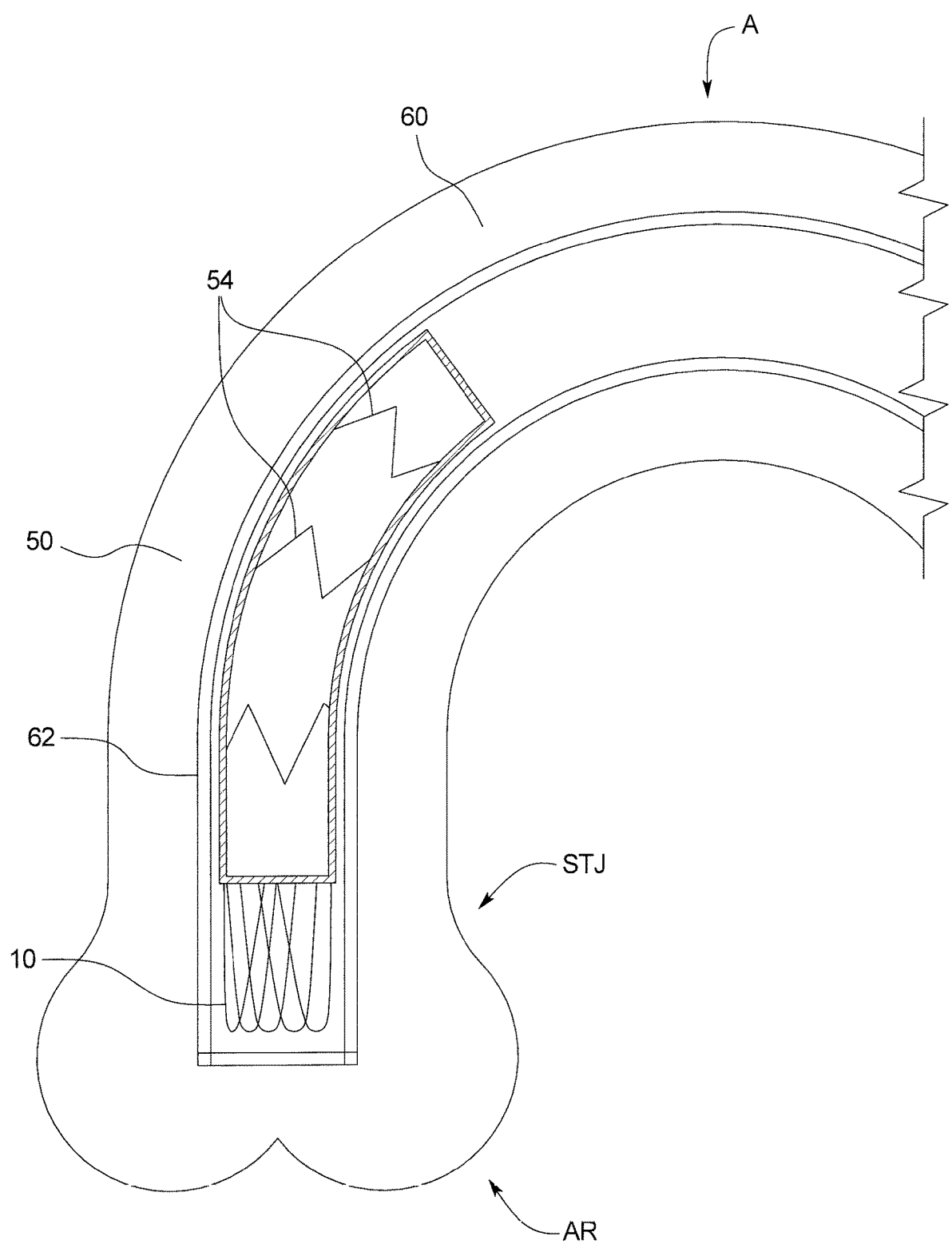
FIG. 6 is a view of a stent graft in use in a body lumen.

The physician may then access a patient's aorta A through a variety of methods, such as the well-known Seldinger technique. For example, the physician may insert the delivery system 60 with the stent graft 50 into the femoral artery. The stent graft 50 and delivery system 60 may then be advanced along the femoral artery towards the heart. Eventually the proximal end of the delivery system 60 will reach the ascending aorta as shown in FIG. 6. The delivery system 60 may be positioned such that the second and third sections 13, 14 of the stent 10, including the twists 23 are positioned just proximal to the sinotubular junction STJ and extending into the aortic root AR. The first section 12 of the stent 10 along with the rest of the stent graft 50 may therefore be positioned to extend just distal to the sinotubular junction STJ into the ascending aorta.

Figure 7:
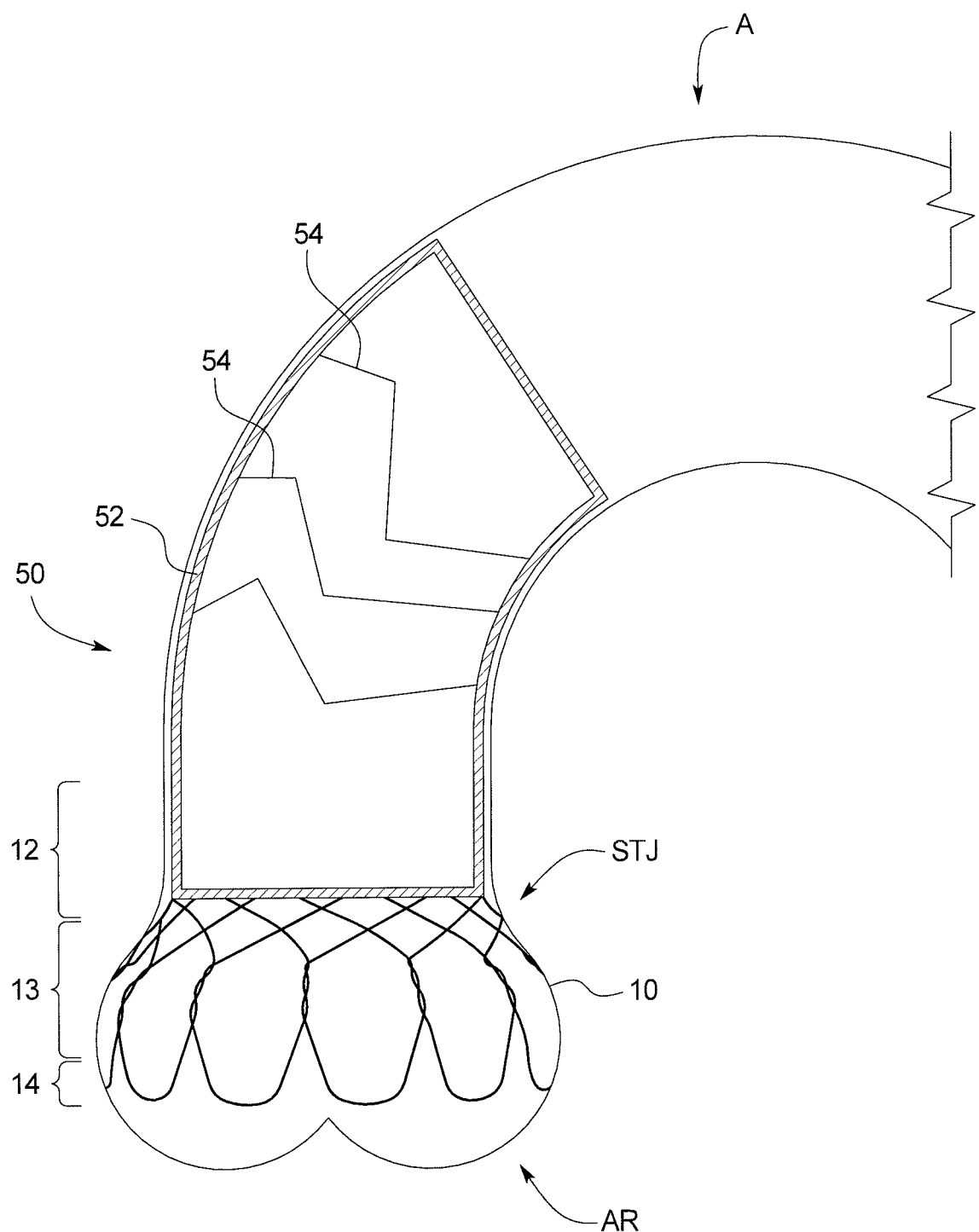
FIG. 7 is another view of a stent graft in use in a body lumen.
Figure 8:
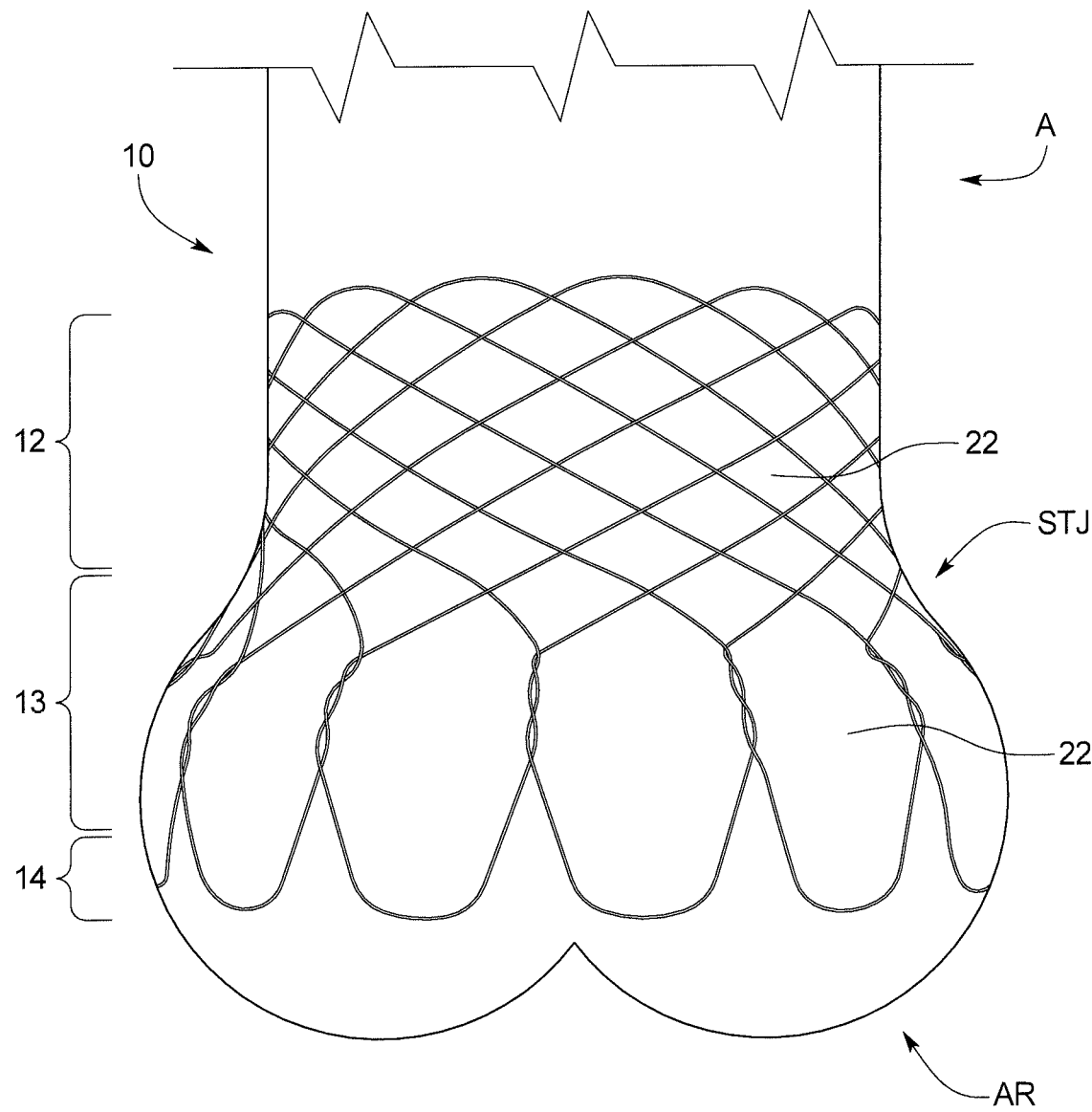
FIG. 8 is a partial view of a stent graft in use in a body lumen with the graft omitted for clarity.

Next, the delivery catheter 62 may be retracted distally while the stent graft 50 is maintained in position, thus freeing the stent graft 50 from the confines of the delivery catheter 62 and allowing the stent graft 50 to expand as shown in FIG. 7. As can be seen in FIG. 7 (and in FIG. 8 showing the stent 10 without the graft 52 and body stent 54), the second and third sections 13, 14 of the stent 10 (including the twists 23 of the second section 13) expand into the aortic root AR, thus allowing the entire stent graft 50 to be more securely placed near the sinotubular junction STJ with limited fear of migration. Further, since the graft 52 does not extend through the second section 14 of the stent 10, the enlarged cells 22 of the second and third sections 13, 14 and the twists 23 in the second section 13 allow for sufficient blood profusion to the coronary arteries, whereas smaller cells may cause undesirable blockage in the aortic root AR. Since the first section 12 of the stent 10 has a tighter pitch, the accompanying greater radial force allows the stent graft 50 to sufficiently support the weakened or ruptured section of the aorta A. Further, since the graft 52 extends distally from the sinotubular junction STJ, the graft 52 may provide the necessary sealing for an aneurysm or dissection right at or near the sinotubular junction STJ.

While the embodiments disclosed above are primarily discussed for use in the aorta and particularly near the sinotubular junction of the aorta, the disclosure is not so limited. The embodiments may be used in a variety of ways and in a variety of body lumens as desired.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:
1. A stent, comprising:
 a plurality of intersecting elongated members arranged to form a plurality of cells, the plurality of cells defining an elongated tube with a lumen running therethrough, wherein the elongated tube comprises first, second, and third sections, the first section having a substantially constant first diameter and the third section having a substantially constant second diameter that is larger than the substantially constant first diameter of the first section, wherein the diameter of the second section transitions from the first diameter to the second diameter, wherein the diameter of the second section transitions from the first diameter to the second diameter via a concave curvature extending proximally from the first section and a convex curvature extending proximally from the concave curvature to the third section,
 wherein a proximal end of the third section of the stent comprises a plurality of rounded ends formed by the plurality of intersecting elongated members, wherein each of the plurality of cells within the first section have a pitch that is tighter than each of the plurality of cells within the second and third sections, and wherein in the second section, the plurality of intersecting elongated members comprises a plurality of pairs of elongated members, wherein each pair of elongated members comprises two adjacent elongated members that define a side of two adjacent cells and are twisted axially around each other to form a twist between each of two adjacent elongated members.

2. The stent of claim 1, wherein each of the twists has no free ends.

3. The stent of claim 2, wherein each of the twists extend from a proximal end of the first section to a distal end of the third section.

4. The stent of claim 3, wherein the twists have a proximal end and distal end and the distal ends of each twist are at a proximal apex of a cell of the first section.

5. The stent of claim 2, wherein each of the twists comprises a plurality of twists.

6. The stent of claim 1, wherein the second and third sections have a curvature configured to conform to a curvature of a body vessel.

7. A stent graft, comprising:

a plurality of intersecting elongated members arranged to form a plurality of cells, the plurality of cells defining an elongated tube with a lumen running therethrough, wherein the elongated tube comprises first, second, and third sections, the first section having a substantially constant first diameter and the third section having a substantially constant second diameter that is larger than the substantially constant first diameter of the first section, wherein the diameter of the second section transitions from the first diameter to the second diameter, wherein the diameter of the second section transitions from the first diameter to the second diameter via a concave curvature extending proximally from the first section and a convex curvature extending proximally from the concave curvature to the third section, wherein a proximal end of the third section of the stent comprises a plurality of rounded ends formed by the plurality of intersecting elongated members, wherein each of the plurality of cells within the first section have a pitch that is tighter than each of the plurality of cells within the second and third sections, and wherein in the second section, the plurality of intersecting elongated members comprises a plurality of pairs of elongated members, wherein each pair of elongated members comprises two adjacent elongated members that define a side of two adjacent cells and are twisted axially around each other to form a twist between each of two adjacent elongated members; and a tube of graft material covering a portion of the stent from adjacent a distal end of the twists to a distal end of the stent.

8. The stent of claim 7, wherein each of the twists has no free ends.

9. The stent of claim 8, wherein each of the twists extend from a proximal end of the first section to a distal end of the third section.

10. The stent of claim 9, wherein the twists have a proximal end and a distal end and the distal ends of each twist are at a proximal apex of a cell of the first section.

11. The stent of claim 8, wherein each of the twists comprises a plurality of twists.

12. The stent of claim 7, wherein the second and third sections have a curvature configured to conform to a curvature of a body vessel.

* * * * *